United States Patent [19]

Noble

[11] Patent Number: 4,896,662

[45] Date of Patent: Jan. 30, 1990

[54] SEALING DEVICE FOR INTRODUCING CEMENT INTO A BONE CANAL

[75] Inventor: Philip C. Noble, Houston, Tex.

[73] Assignee: Pfizer Hospital Products Group, Inc., New York, N.Y.

[21] Appl. No.: 126,451

[22] Filed: Nov. 30, 1987

[51] Int. Cl.⁴ .............................................. A61B 17/56
[52] U.S. Cl. ........................................ 606/94; 606/92
[58] Field of Search .......... 128/92 V, 92 VV, 92 VP, 128/92 VQ, 303 R; 623/16, 18, 22, 23

[56] References Cited

U.S. PATENT DOCUMENTS

| | | | |
|---|---|---|---|
| 4,245,359 | 1/1981 | Stuhmer | 623/18 X |
| 4,276,659 | 7/1981 | Hardinge | 623/18 X |
| 4,293,962 | 10/1981 | Fuson | 128/92 V X |
| 4,338,925 | 7/1982 | Miller | 604/61 X |
| 4,462,394 | 7/1984 | Jacobs | 128/92 VP |
| 4,466,435 | 8/1984 | Murray | 128/92 VQ X |
| 4,488,549 | 12/1984 | Lee et al. | 623/16 X |
| 4,627,434 | 12/1985 | Murray | 128/303 R |
| 4,645,504 | 2/1987 | Byers | 623/16 X |

FOREIGN PATENT DOCUMENTS

| | | | |
|---|---|---|---|
| 6408 | 1/1980 | European Pat. Off. | 128/92 VP |
| 0073604 | 3/1983 | European Pat. Off. | |
| 0139520 | 5/1985 | European Pat. Off. | |

Primary Examiner—Robert A. Hafer
Assistant Examiner—Kevin G. Rooney
Attorney, Agent, or Firm—Pennie & Edmonds

[57] ABSTRACT

A proximal femoral sealing device is disclosed for use in the application of bone cement under pressure to a surgically prepared medullary canal of a femur prior to the implantation of a hip prostesis. The proximal femoral sealing device is formed of a generally solid body member with a passageway and a flexible annular wall member extending from the body member. The sealing device has an anatomically shaped outer surface, corresponding to the exposed endosteal surface of a prepared medullary canal. A chamber defined by a flexible annular wall and the body member opens into the medullary canal. In turn, the passageway communicates with the chamber and permits insertion of a cement nozzle therethrough into the chamber. In operation, the proximal femoral sealing device is placed within the proximal end of a surgically prepared medullary canal. The canal and chamber of the sealing device are filled with cement resulting in the expansion of the flexible annular wall member against the exposed endosteal walls of the medullary canal by cement pressure within the chamber thereby forming a pressure seal. The escape of cement through the open end of the excavated medullary canal is prevented via this pressure seal insuring that the applied cement is properly pressurized and that the medullary canal is prepared for implementation of the prosthetic device. A method of providing cement under pressure to the exposed endosteal surface of a medullary canal is also disclosed using this proximal femoral sealing device.

24 Claims, 3 Drawing Sheets

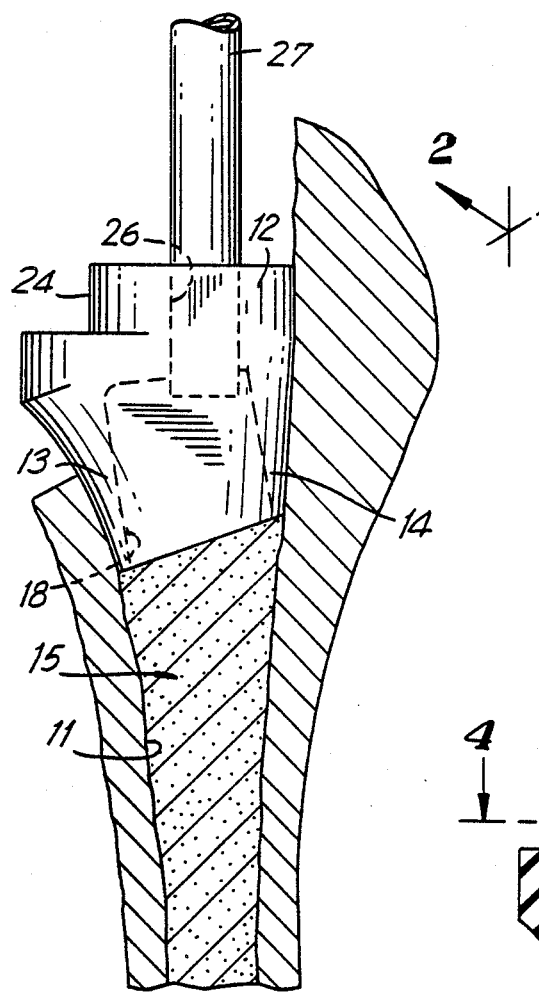
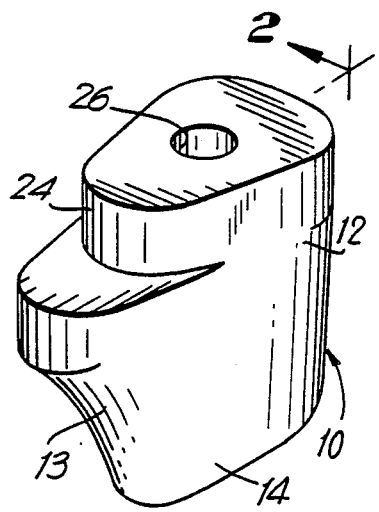
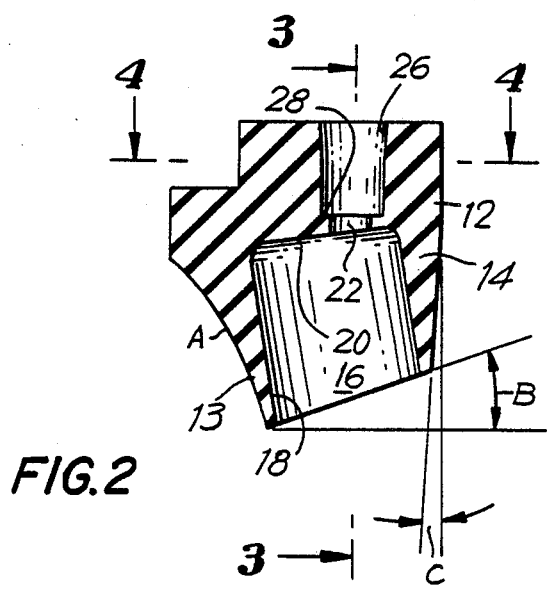
FIG. 6
FIG. 1
FIG. 2

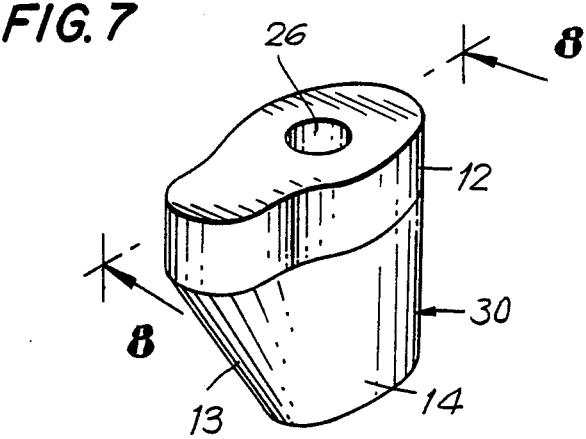
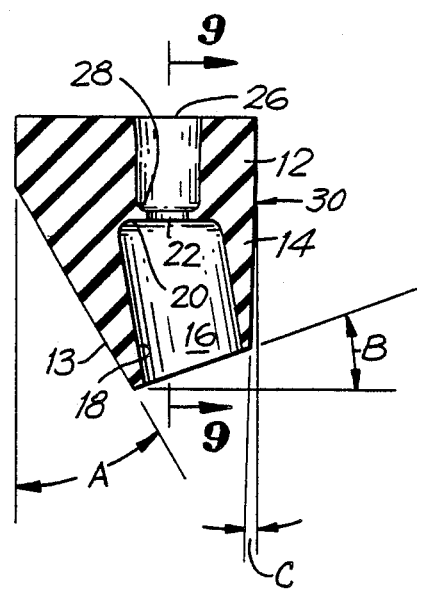
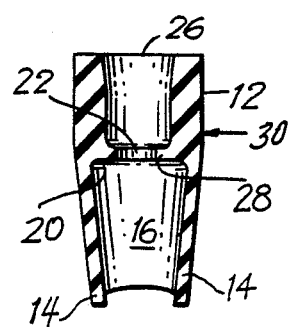
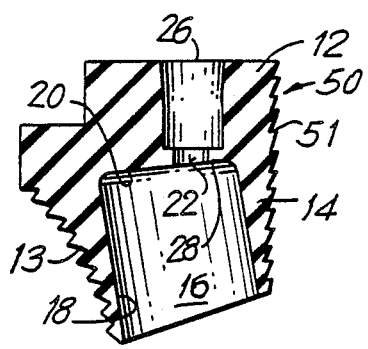

SEALING DEVICE FOR INTRODUCING CEMENT INTO A BONE CANAL

FIELD OF THE INVENTION

This invention generally relates to an apparatus and method for injecting bone cement under pressure into a bone canal. The cement allows for implantation of a prosthetic device.

BACKGROUND OF THE INVENTION

There are from 80,000 to 150,000 total hip arthroplasty (THA) procedures completed each year in the United States. Worldwide, there are over 300,000 to 400,000 THA procedures performed each year. This procedure, whether unilateral or bilateral, is performed to relive a variety of objective signs of disability, such as to relieve pain and to increase or preserve mobility. A diagnosis which suggests THA for treatment may include, for instance, primary or secondary osteoarthritis, congential dysplasia, polyarthritis, including rheumatoid arthritis, and ankylosing spondylitis, previous unsuccessful joint surgery and Paget's Disease of the bone. The indications for bilateral THA include primary idiopathic bilateral monoarticular osteoarthritis, primary generalized osteoarthritis, ischemic necrossis of the femoral head with secondary acetabular failure, and secondary degenerative osteo arthritis resulting from congential dysplasia. Additional factors such as flexion deformity of more than 30°, one hip fixed in addjuction, the other fixed in abduction (causing the patient to fall from lack of balance), leg shortening, acetabular protrusion, age and other factors should be considered prior to considering a bilateral procedure.

Generally stated, THA is an operation where the ball and socket joint which forms the natural hip is replaced by artificial materials. The development of THA components has occurred over the last three decades. The THA procedure and related components are described in the publication entitled The Howmedica Precision Hip System, Copyrighted 1986 by Howmedica, Inc., which publication is hereby incorporated by reference in its entirety. In the procedure carried out today, the spherical end of the femur is removed and replaced with an artificial metallic implant. The stem to which the ball is attached (via a "neck") fits down the middle of the femur in the surgically prepared medullary canal and is located in place by bone cement. The spherical head of the femoral component is placed into the socket of the acetabular component forming a total replacement of the hip joint (both components are commercially available as the A.T.S. ® Total Hip System and The P.C.A. ® Total Hip System from Howmedica, Inc.).

In preparing the femoral medullary canal for implantation, the steps after resection (removal) of the head of the femur include reaming, broaching and cleaning out (lavage and brush) the medullary canal. This area of the bone contains the bone marrow which also fills spaces in cancellous bone.

The femoral canal typically is prepared from its distal portion ot he proximal portion, i.e., in a retrograde manner. The femoral canal may be opened with any standard blunt surgical awl or manual reamer. The surgeon, in cleaning the medullary canal, will progressively use larger reamers until the reamer contacts the harder bone at the cortex of the isthmus. Broaches or rasps are utilized in order to accommodate the appropriate implant with neutral, posterior and anterior implants. At the proximal end (with reference to the surgeon) of the medullary canal, the proximal broach is used. This broach has a smooth tip and middle portion with its cutting surface being proximal. This instrument has five functions: it provides the precise canal size for the cement mantle; it is used to position the calcar reamer; the flat plane can be used to provide the final osteotomy level and it is used in trial reduction to assure proper fit and as a trail since it is sized to correspond to the correct femoral component pluys cement mantle. The prepared (reamed and broached) medullary canal is then cleaned and dried.

Prior to introducing cement into the intramedullary plug is typically utilized to effectively create a block at the isthumus (a lower portion fo the medullary canal at which it has a narrow diameter) to make the upper femur a closed system. The plug reduces the amount of debris forced up the canal when cement is introduced and it insures pressurization thus helping to provide stem fixation.

The actual bone cemen tis not a glue but is a filler and enables the mechanical interlock of bone on one side to a prosthesis on the other. The material used in creating the bone/prosthesis interface which is presently preferred is polymethylmethacrylate (also known as PMMA), one of a family of the polymers known as acrylics and is familiar commercially as Plexiglass ® and Lucite ®. This material is "cold-curing" or "self-polymerizing" thus enabling its use in the THA procedure. A preferred cement utilized today is Surgical Simplex ® P Bone Cement (commercially available from Howmedica, Inc.), which is a co-polymer of polymethylmethacrylate and styrene. This amterial has a compressive strength ranging from 9,000 to about 13,800 pounds per square inch, a tensile strength ranging from about 3,600 to 6,800 psi; a shear strength ranging from 5,700 to 7,000 psi and a modulus orf elasticity ranging from 2.3 to $3.8 \times 10^5$ psi.

A variety fo factors and variables will influence the effectiveness fo the cement used in the THA Proceuree, such as: the rate of mixing; the porosity of the cement formed during mixing; the additives utilized in conjunction with the bone cement such as the addition of antibiotics to the cement mix; polymer shrinkage; the THA procedures itself; the set time; the powder to liquid ratio; tprepartion of the bone surface including the presentation of debris such as blood, bone chips or powder and other tissue; the delay in aopplying the cement; the pressure at which the cement is applied into the medullary canal and the cement thickness. The pressure at which the cement is supplied to the medullary canal is one of the most significant factors in the success of the implant.

In the early days of prosthetic surgery, the mixed cement was placed into the femur and simply manually pressed into place. No matter how much pressure is manually applied sufficient pressure to insure a good interface between cement and bone could not be assured. Furthermore, use of this technique in the past often resulted in a femoral canal that was incompletely filled with cement.

The cement is now typically provided to the interior exposed endosteal surface of the medullary canal with a bone cement gun (commercially available, for example, as the Exeter ® Cement Gun & Syringe from Howmedica, Inc.). In the commercially available cement guns, a nozzle is fitted to the gun and delivers the cement under pressure to the canal. The liquid and powder which comrpiess the cement may be mixed prior to placement in the cement gun with commercially available systems (i.e., the Mix-Kit ® Systems or in the Simplex Enhancement Mixer ® commercially available from Howmedica, Inc.) so that it may be applied in a viscous or liquid state.

After the bone cement is applied to the exposed endosteal surface of the prepared medullary canal, the implant is inserted into the canal. The cement, which polymerizes and hardens in the space between the bone and the implant, functions as a luting agent. The quality of the fixation is greatly enhanced by the mechanical interlocking of the cement with tthe porous trabecular structure of the cancellous bone of the wall of the intramedullary canal and with any pores, dimples, elevations, keys, etc. provided ont eh surface of the implant.

Fixation of surgical implants with polymethylmethacrylate bone cements within intramedullary canals has been practiced with great success for many years. On occasion, however, problems associated with the premature lossening of the implant in use have been observed. One explanation for these loosening problems is an inadequate penetration fo the bone cement into the cancellous bone of the intramedullary canal wall. It is known that this penetration can be improved by pressurizing the viscous or liquid bone cement within the intramedullary canal so as to work the cement deeply into the cancellous bone fo the canal wall before it hardens. Thus, it is well known to utilize an intramedullary plug as described above to prevent passage of cement distally (with reference to the surgeon) of its desired location within the intramedullary canal (see, for example, U.S. Pat. Nos. 4,245,359; 4,276,659 and 4,293,962 and European Pat. No. 6408).

Pressurization can be further improved to some but, as noted above, a limited extent by finger packing by the surgeon. Compactors have also been used to compress and pressurize bone cement applied to an intramedullary canal. However, the use of a compactor requires the addition of a distinct, time-consumign step to the surgical procedure, with the results being operator intensive, i.e., the extennt of pressurization achieved depends upon the axial force exerted by the surgeon.

Additionally, it is known to equip the nozzle of a bone cement extruder with a restrictor (e.g., the Miller Bone cement Injector Restrictor Set; Zimmer, USA; Warsaw, Ind.) made of a solid resiliebnt material to block the flow of cement between the nozzle and the bone through the open end of the prepared intramedullary canal. However the quality fo the seal obtained is limited because the fits of such a frestricter againt the bprepared bone is more in the nature of a line contact at the open end than a surface-to-surface contact and, furthermore, the quality of the seal will be reduced when the restricter is unable to completely fill any irregularities in the bone against which it fits. Again, the extent of pressurization achieved depends upon the axial force exerted by the surgeon.

Devices simlar to the Miller device have been utilized wherein the upper or proximal portion of the sal is more flexible than on the Miller seal in order to accommodate a wider variety of openings in the medullary canal. This type of seal remains within the medullary canal by virtue of axial pressure fromt eh surgeon holding it in place or alternatively by its fit wtihin the prepared medullary canal. The pressure of the cement added to the bone would oppose, however, the fit of this type of plug pushing it in a direction out of the proximal end of the medullary canal.

In addition, U.S. Pat. No. 4,462,394 discloses an intramedullary canal seal which comprises a hollow tube adapted to slidingly receive the nozzle of a bone cement extruder and an inflatable cuff surrouidng the tube and a means to inflate the cuff. The inflated cuff is said to form a seal against the wall of the intramedullary canal, threby preventing escape of cement through the open end of the prepared canal. In European Patent Application No. 82304353.4, a device is disclosed which is designed to fit over and seal the opening of a cavity in a bone to allow pressurization of cement in the cavity. This device is described as having an aperture for sealingly receiving a cement delivery nozzle and the seal member itself may be a balloon seal, which is inflatable and expandable, or a solid material, either of which embodiments is urged or pressed against the opening of the bone by force of the barrel of the cement delivery gun or an additional abutment means. This device does not fit within the intramedullary canal but instead seats on top of the proximal end of the canal. the cement sealing effect is achieved by the force of holding this eal against the opening of the bone and not by any force exhibited form the cement against the seal.

Cement restrictors have also been disclosed for use in conjunction with fixing the acetabular portion of the hip prosthesis as in U.S. Pat. Nos. 3,889,665 and 3,886,248. These restrictors do not provide for the use of the cement pressure itself to hold the seal in place during application of the bone cement.

I have invented a sealing device which avoids the aforementioned problems and provides for much greater penetration of cement into the bone.

SUMMARY OF THE INVENTION

The present invention is directed to an apparatus for introducing cement into a bone canal through an opening in the bone, comprising body member having a passageway therethrough for passage of cement; generally annualar wall emmber extending from the body member and defining an outer surface at least a portion of which is configured and dimensioned so as to be capable of extending into the bone canal and generally seal the bone opening; and chamber defined by the annular wall member, the chamber communicating with the passageway and with the bone canal such that cement, upon its introduction into the bone canal, will also fill the chamber so as to aid in maintaining the seal.

Preferably the apparatus is suitable for injecting cement into the bone canal and the generally annular wall member is flexible and together with the body member defnes a generally continuous outer surface which is configured and dimensioned such that at least a portion of the outer surface corresponds anatomically to a portion of the bone canal adjacent the opening so as to be capable of extending into the bone canal and sealing the bone opening. The chamber defined by the annular wall member and the body member communicates with the passageway and with the bone canal such that cement upon its injection into the bone canal will also fill the chamber so as to expand the flexible annular wall member and thus maintain the seal and aid in the penetration of cement into the bone within the canal.

In a preferred embodiment, the present invention relates to a proximal femoral sealing device for seating within the medullary canal of a prepared proximal end of a femur and for injecting cement under pressure into the medullary canal, comprising body member having a passageway therethrough for passage of cement; generally flexible annular wall member extending from the body member and defining with the body member an outer surface which is anatomically shaped and conforms generally along the vertical and horizontal axes of the body member to the exposed internal endosteal surface shape of the proximal end of the medullary canal of the femur; and chamber defined by the flexible wall member and the body member, the chamber opening onto and communicating at one end with the proximal end of the medullary canal, the other, opposite end opening onto and communicating with the distal end of the passageway, the chamber further having a generally rounded-trapazoidal cross-sectional configuration defined by the flexible wall member which is capable of expanding under pressure of cement within the chamber against the exposed internal endosteal surface fo the medullary canal so as to form a pressurization cement seal.

The anatomically shaped outer surface can generally correspond to the otuer surface shape of a broach utilized to expose the endosteal surface of the medullary canal or to the natural internal surface shape of the medullary canal. In an alternative embodiment, the anatomically shaped outer surface further comprises a plurality of ridges which are dimensioned and configured so that leading edges thereof contact the exposed internal endosteal surface.

Also the proximal end fo the anatomically shaped otuer surface preferably is wider than the distal end along a cross-section of the vertical axis of the seal. The portion of the anatomicallyshaped outer surface adjacent the alteral side of the medullary canal can be aligned at an angle from about 1° to about 4° in from the vertical axis of the seal towards the wall of the medial side fo the medullary canal. The portion of the substantially anatomically shaped otuer surface of the medial side of the medullary canal can be straight to curved, for example, with a radius of from about 3–20 inches from the proximal to distal end of the substantially anatomically shaped outer surface.

In a preferred embodiment, the wall member is thicker at the proximal end of the chamber than at the distal end of the chamber. In addition, the wall member tapers to reduce in thickness fromt he proximal end to the distal end.

The substantially anatomically shaped outer surface which ends at the distal end of the seal can be aligned at an angle fo about 0° to about 20° away from the horizontal axis of the seal toward the proximal end of the seal with the shorter wall length being angled towards the proximal end. The lateral portion of the wall member and medial portion of the wall member can be aligned at about 10° from the vertical axis fo the seal, with the lateral and medial portions being aligned parallel to each other and with the end of the medial portion of the wall being more proximally located to the vertical axis than the lateral portion fot he wall. The anterior and posterior portison of the wall member between the medial and lateral portions can be aligned on the horizontal axis at an angel from about 10° to about 12° away fromt he transverse axis, with the anterior and posterior portiond being closer together at the medial portion that at the lateral portion.

The passageway is preferably centrally disposed in the body member and is dimensioned and configured to receive a nozzle for injection of cement. The passageway preferably is cylindrical in shape. the passageway narrows to form a gasket-seal so as to restrain a cement nozzle inserted through the passageway. This gasket-seal is disposed adjacent the proximal end of the chamber or can be disposed betweent he proximal and distal ends of the passageway. Also a medial portion of the body member can be inset from the medial portion of the anatomically shaped outer surface.

It is preferred that the body member and flexible annular wall member are formed of a medical grade elastomer and, in particular, they can be integrally formed of silicone.

The present invention is also directed to a method for introducing cement into a bone canal comprising: preparing an opening in the bone; positioning a sealing device according to the present invention into the bone canal through the opening; inserting a cement nozzle through the passageway and into the chamber of the sealing device; and providing cement under pressure to the bone canal and to the chamber of the sealing device whereby the walls of the chamber, being under presusure, expand against the exposed surface of the bone canal thereby forming a pressure seal against the exposed surface enbling the cement to completely fill the medullary canal under pressure.

In accordance with a preferred embodiment, the present ivne;ntion is also related to a method for providing cement under pressure to the exposed endosteal surface of a medullary canal of a femur, comprising exposing the endosteal surface of a medullary canal of a femur, inserting a proximal femoral sealing device according to the present ivn;ention into the proximal portion of the medullary canal; inserting a cement nozzle through the passageway and into the chamber of the sealing device; and injecting cement through the cement nozzle under pressure into the medullary canal and into the chamber of the sealing device such that the flexible annular wall member, being under pressure, expands against the exposed endosteal surface so as to form a pressure seal against the exposed surface enabling the cement to completely fill the medullary canal under pressure.

The cement is provided under pressures ranging from at least about 30 to about 100 psi and preferably the cement has an average pressure of about 50 psi while filling the medullary canal. The pressure is sufficient to permit permeation fo the cement into the exposed endosteal surface to a depth of at least about 5 millimeters. After the sealign device is removed from the proximal end of the medullary canal of the femur upon filling of the medullary canal under pressure, a femoral stem is implanted therein. In an alternative embodiment, a bone plug is inserted into the distal portion of th emedullary canal prior to inserting said sealing device. Also if desired, the medullary canal can be filled with some cement prior to inserting the proximal femoral sealing device.

According to the method of this invention, the increased cement pressure on the seal's flexible walls relieves the surgeon from havving to use as much force as is required with other seals to maintain the seal in position within the medullary canal. This further permits increased pressurization fo the cement application within the medullary canal. Increased pressure of cement within the medullary canal helps to insure better and more secure prosthetic implant anchoring. In addition, the flexibility of the walls of the seal permit a better and more uniform seal against the endosteal surface of the medullary canal without regard to minor irregularities in shape which may be present in different patients. This ivnetnion also provides for a novel method for delivering cement under pressure to the exposed endosteal surface of a medullary canal in such a manner that the depth of cement penetration is significant and assists in generating excellent prosthesis anchoring.

It is also within the scope of this invention that some cement can be introduced into the canal prior to positioning the sealing device into the medullary canal and thereafter the procedure described above canb e followed. If desired, the seal can additionally be secured in plasce with external axial pressure (i.e., by hand or mechanical means) so as to provide additional assurance of the positioning of the seal when providing the cement under high pressure.

BRIEF DESCRIPTION OF THE DRAWINGS

The present invention is described in detail below with reference to the drawings wherein:

FIG. 1 is a perspective view of a proximal femoral sealing device according to the present ivne;ntion.

FIG. 2 is a cross-sectional view fo the proximal femoral sealing device taken along the lines 2—2, the transverse axis fo the device, of FIG. 1.

FIG. 6 is a side elevational view partially in cross-section illustrating the positioning of the proximal femoral sealing device of FIG. 1 within the proximal end of the femoral intramedullary canal.

FIG. 7 is a perspective view of an alternative embodiment of a proximal femoral sealing device according to the present invention.

FIG. 8 is a cross-sectional view of the proximal femoral sealing device taken along the lines 8—8, the transverse axis of the deivce, of FIG. 7.

FIG. 9 is a cross-sectional view of the proximal femoral sealing device as shown in FIG. 1 taken along the lines 9—9, the vertical axis of the device, of FIG. 8.

FIG. 10 is a cross-sectional view of a second alternative embodiment of the proximal femoral sealing device according to the present invention.

DETAILED DESCRIPTION OF THE INVENTION

Figure 3:
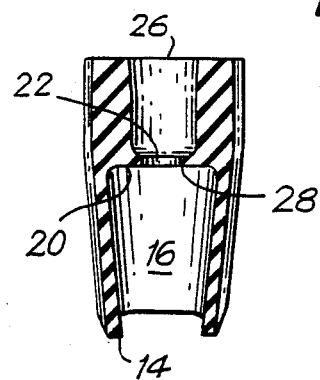
FIG. 3 is a cross-sectional view of the proximal femoral sealing device as shown in FIG. 1 taken along the lines 3—3, the vertical axis of the device, of FIG. 2.
Figure 4:
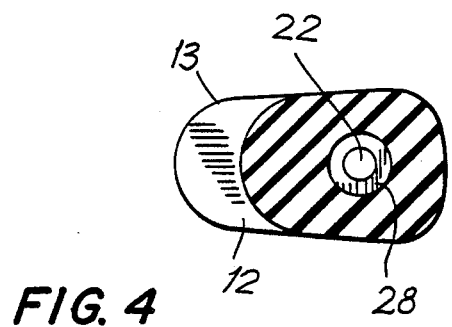
FIG. 4 is a cross-sectional view of the proximal femoral sealing device as shown in FIG. 1 taken along the lines 4—4, the horizontal axis of the device, of FIG. 2.

In the description which follows, any reference to either direction or orientation is intended primarily and solely for purposes of illustration and is not intended in any way as a limitation of the scope of the present invention. Also, the particular embodiments described herein, although being preferred, are not to be considered as limiting of the present invention. Furthermore, like parts or elements in the various drawings hereto are identified by like numberals for ease of reference.

A proximal femoral sealing device 10 of the present invention is shown in FIGS. 1-5. Sealign device or seal 10 is formed of a body member 12 and an annular wall member 14 that extends from the body member as shown more clearly in FIG. 2. The seal 10 has an outer substantially anatomically shapes surface 13 which conforms, along the vertical and horizontal axis fo the seal 10, to the internal exposed endosteal surface 11 shape of the proximal end of the surgically prepared medullary canal of the femur as shown in FIG. 6. The anatomically shaped surface 13 is defined by wall portions 14 which are flexible and are capable fo expanding under pressure against the internal exposed endosteal surface of the medullary canal so as to form a pressurization seal. The seal 10 can be formed of various sizes to permit insertion within the proximal end of the medullary canal so as to engage the exposed endosteal surface which would surround the anatomically shaped surface upon its insertion into the proximal end of the medullary canal.

The proximal femoral seal 10 of the present invention also has an internal chamber 16 defined by the inner surfaces 18 of flexible portions of the annular wall member 14 (which defines the anatomically shaped outer surface 13) and inner surface 20 of body member 12. At one end, the internal chamber 16 opens onto and communicates with a proximal end of the medullary canal as shown in FIG. 6. At the other opposite end, the internal chamber opens onto and communicates with the distal end 22 of a cement nozzle entry port or passageway 26 in body member 12. The internal chamber 16 has a generally rounded-trapazoidal cross-sectional configuration which is defined by the flexible portions of the wall as shown in FIG. 3.

Figure 5:
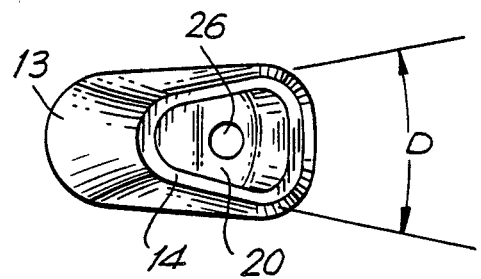
FIG. 5 is a bottom view of the proximal femoral sealing device of FIG. 1.

The body member 12 of proximal femoral seal 10 also preferably has an upper portion 24 which is lcoated on the vertical axis of lines 3-3 of the seal 10 above the anatomically shaped surface 13. The upper portion 24 is contiguous with the anatomically shaped surface and also has a generally rounded-trapazoidal cross-sedctional configuration along the horizontal axis of lines 4-4 of the seal 10 as shown in FIG. 5. the upper portion 24 also includes the cement nozzle entry port 26 which has a smaller distal end 22. The cement nozzle entry port traverses the upper portion along the vertical axis fo the proximal femoral seal 10 with the distal end 22 of the cement nozzlwe entry port 26 communicating with the internal chamber 16. The proximal femoral seal 10 preferably is formed integrally as a single unit, i.e., by known molding techniques, from a medical grade elastomer such as silicone rubber.

It is also preferred that the substantially anatomically shaped surface 13 generally corresponds to the outer surface shape of a broach utilized to prepare the medullary canal and expose the endosteal surface 11. It is within the scope fo this ivne;ntion that a variety fo sizes of broaches may be used and that the proximal femoral seal preferred embdoiment shown in FIGS. 1-6 and 10 will preferably accommodate a larger size broach whereas the proximal femoral seal preferred embodiment shown in FIGS. 7, 8, and 9 would preferably accommodate smaller size broaches utilized typically where the femur or medullary canal is of a smaller size.

In both oepration and principle, however, both of these designs are equal. The two embodiments as shown in FIGS. 1 through 10 would, by virtue of their anatomic shapes, accommodate most, if not all, prepared medullary canals. FIG. 6 shows a cross-sectional view of the seali 9n polace within a medullary canal with a cement gun nozzle 27 located through the passageway 26 and into the interior chamber 16. It is clear from this view that the seal could also be accommodated with a larger opening of the proximal end merely by fitting it down further into the medullary canal 15 or alternatively fitting it within a smaller opening by placing it higher up the canal where the opening is smaller. It is also within the scope fo this invention ]that the substantially anatomically shaped surface 13 generally corresponds to the natural internal endosteal surface shape 11 of the medullary canal 15. In this manner, it is clearly within the scope of this ivnention that this seal would be utilizable in a medullary canal which is prepared without the use of a broach.

As shown in FIG. 10, another alternative preferred embodiment 50 of this inve;ntion, the substantially anatomically shaped surface 13 is not smooth as in the embodimebnt FIGS. 1-9 but rather comprises concentric ridges 51 alogn the horizontal axis of the outer surface. In the operation of a seal having this ridged surface, the crest of the ridges are the portions of the sealing deivce which come in contact with the exposed endosteal surface 11 of the proximal ebnd fo the medullary canal 15. It is these crests which are forced against he exposed endosteal surface to provide a gripping effect upon an increase in cement pressure from within the internal chamber 16 of the sealing device 50 during the cement filling operation. In both this and the embodiments of the proximal femoral seal described above, the proximal end on the vertical axis of the substantially anatomically shaped ridged surface 51 is wider than the distal end when viewed along a cross-section of the vertical axis of the seal (from the medial to the lateral edges).

In all of the embodiments, 10, 30 and 50 the general relationship of the walls and internal chamber to each other are generally the same. However, they may be modified by one of ordinary skill in the art to accommodate a variety of circumstances and surgical situations so long as the sealign deivce has a substantially anatomical shape and an internal chamber with annular wall member that will flex outwardly under increased cement pressure. In the preferred embodiments, however, various angles and relationshipes are described for the purpose of illustration.

In the preferred proximal femoral sealing devices 10, 30 and 50 of FIGS. 1-10 the annular wall member 14 defining of the substantially anatomically shaped surface ranges from a straight surface to one which is curved (angle A), for example, with a radius of from about 3-10 inches fromt he proximal to the distal end of the substantially anatomically shaped surface 13.

In addition, the wall defining the substantially anatomically shaped surface 13 is thicker at the proxmal end of the internal chamber 16 that at the distal end of the internal cavity. The distal end of the internal chamber 16 communicates with the medullary canal. It is seen in FIGS. 1-10 that this wall tapers to reduce in thickness from the proximal end to the distal end of the sealing device 10, 30 and 50. It is also seen in FIGS. 1-10 that the wall of the substantially anatomically shaped surface 13 which ends at the distal end of the seal is aligned at an angel of about 20° from the horizontal axis of the seal towards the proximal end of the seal (angle B). the shorter portion of the annular wall length is angled towards the proximal end. It is also within the scope of this invention that the sealing device 10, 30 and 50 would be perfectly operable with the walls being aligned parallel to each other on the horizontal axis at the distal end of the sealing deivce 10, 30 and 50. However, while not loosing any strength inherent in the sealing device by canting the annular wall member up at a 20° angle, it is possible to expose a greater amount of the exposed endosteal surface 11 to cement during the procedure by which the cement is applied to the medullary canal 15.

It is also seen in FIGS. 2, 8 and 10 that the lateral wall portion and medial wall portion of the internal chamber are aligned at about 10° from the vertical axis of the seal (see angle C). These portions of the wall member 14 are also aligned parallel to each other with the end of the medial portion of the wall member 14 being more proximally located to the vertical axis than the lateral portion of the wall. In this manner, the wall thickness is essentially the same on either the medial or lateral side of the interior chamber 16 thereby allowing an equal tapering of the wall to be achieved from the proximal to the distal end of the seal. This in turn permits equal expansion of the wall member 14 upon pressurization.

In order to accommodate for the natural anatomical shape of the excavated medullary canal 15, it can also be seen in FIGS. 1, 3 and 5 that the anterior and posterior wall of the internal cavity between the medial and lateral portions fo the wall are aligned on the horizontal axis at an angle ranging from about 10° to about 12° away from the transverse axis (angle D), with their walls being closer together at the medial portion of the wall than at the lateral portion fo the wall. It can also be seen from FIGS. 3, 5 and 6 that the internal chamber 16 opening onto the medullary canal 15 is defined solely by the annular wall member 14 of the internal chamber 16. In this embodiment, the cement can easily enter and fill the internal chamber and thereby exert pressure to push out the ananular wall member 14 of the internal chamber 16 against the exposed endosteal surface 11 forming the desired pressure seal.

FIG. 1 also shows that the cement nozzle port 26 is centrally disposed in the proximal end of the sealing device 10 and substantiallyy centrally disposed onthe proximal end of the chamber 16. However, it is also within the scope of this invention that the cement nozzle entry port 26 could be disposed at any location on the top fo the internal chamber 16 so long as adequate support is provided for the cement nozzle 27 on the seal. It can be seen in FIG. 1 that the medial portion of the body member 12 of the upper portion of the seal is insert from the medial wall of the anatomically shaped surface 13. In this fashion, the weight of the seal 10 can be reduced and the inset portion 24 also provides a stepped area upon which additional axial; external force can be applied manually or mechanically so as to retain the seal within the medullary canal 15. It can also be seen that in FIG. 7 the medial portion of the body member 12 of the sealing device 10 may alternatively be formed contiguous with the medial portion of the substantially anatomically shaped surface 13.

FIGS. 1-10 show that the inner surface 20 of the body member 10 also defines the proximal end of the internal chamber 16 having the distal end 22 of passageway 26. In this embodiment, the body member 12 provides additional support for the pressure encountered in the internal chamber thereby insuring that the maximal expansion is encountered in the annular wall 14 of the interior chamber 16 as opposed to the inner surface 20 of the chamber 16 so as to enhance the sealing effect.

In order to accommodate the standard cement nozzles or syringes, the cement gun nozzle entry port 26 of the proximal femoral sealing device 10 is preferably cylindrical in shape. As can be seen in FIG. 2, the cement gun nozzle entry port may also comprise a gasket-seal 28 which also provides an additional means to restrain the cement gun nozzle when it is inserted into and through the cement nozzle entry port 26. This gasket expands when the cement gun nozzle is forced through it, thereby expanding and tightly fitting aroudn the cement nozzle itself. This gasket-seal 28 helps prevent leakage of cement under pressure through the cement gun nozzle port 26 and also assists in securing the cement gun nozzle itself when exposed to the pressurized cement within the internal cavity. The gasket-seal 28 can be located adjacent ot the internal chamber 16,, i.e., directly at the opening to the internal chamber 16, or inset a short distance from the internal chamber 16 as in FIG. 6. The gasket-sel 28 may also preferably be located at any point between the interior chamber 16 and the opening of the cement nozzle entry port 26 at the top, proximal end of the sealing device 10.

The present invention is also directed to use of the sealing device for injecting cement into a bone canal prior to implanation of a femoral prosthesis. After the medullary canal of the femur has been surigically prepared (and preferably reamed with an appropriate broach), the cleaned cancellous bone is essentially ready to be exposed to the bone cement. If desired, an intermedullary plug such as the Seidel plug can be preferably inserted into the canal to prvent passage of cement distally of the plug. The bone cement is then mixed and loaded into a cement gun according to the manufacturer's instructions. The cement gun nozzle is then inserted through the open proximal end of the prepared medullary canal until its distal tip is generally approximate to the plug.

The bone cement is then applied through the cement gun nozzle and as the application continues it proceeds to fill the canal to a desired level. The nozzle is then removed at a point where the cement has filled the canal up to about the proximal opening of the medullary canal. At this point the nozzle is placed into the passageway 26 on the proximal femoral seal 10. The proximal femoral seal 10 is then placed in the proximal end of the prepared medullary canal and additional cement is then injected into the casnal under pressure. Sufficient cement is also added so as to fill the interior chamber 16 of the proximal femoral seal 10 thereby expanding its flexible annular wall 14 outwardly forming a tight pressure seal against the exposed endosteal walls 11 of the proximal end of the medullary canal. The formation of a tight and secure seal by the expanded walls 14 of the prosximal femoral seal 10 against the exposed endosteal walls 11 insures that cement is prevented from escaping through the open proximal end and thus insures that a high degree of pressurization is achieved. After sufficient pressuirization is achieved, the nozzle and proximal seal 10 canb e removed from the canal. It is also within the scope of theis ivnention that the cement nozzle can be placed through the passagway 26 on the proximal femoral seal 10 prior to the cement level reaching the proxiimal end of the medullary canal. Altenratively all of the cement needed can be injected into the canal after the cement nozzle .can be injected into the canal after the cement nozzle is positioned through the passage 26 and the sealing device 10 is inserted into the proximal open end of the medullary canal.

At the completion fo the cement deposit procedure, the nozzle and proximal femoral seal casn be removed simultaneoulsy or separately, i.e., the nozzle may be removed prior to removal of the seal. Becuase of the excellent pressurization of cement resulting form the use of the femoral seal 10 of the present invention, the cement penetrates deeply into the cancellous bone of the medullary canal wall and provides a very strong and stable fixation of the prosthesis. The depth of capillary penetration is, for instnace, shown in the respective figure illustrated in the publication entitled "Innovations In Cementing Techniques In Total Hip Replacement" presented as a Scientific Exhibit at the American Academy of Orthopedic Surgeons 54th Annual Meeting, San Francisco, held on Jan. 22–27, 1987. This figure clearly demonstrates that utilization of the present invention provides a much greater cement penetration depth than other methods utilizing manual pressurization or the solid seal type (Miller) of device. This publication in another figure shows the increased pressure capable with the proximal femoral seal 10 of the present invention as compared to manual techniques and the use of sold seals. Pressure of up to 60 pounds per square inch are shown in this figure. However, pressures of up to 100 pounds per square inch have been achieved with the proximal femoral seal 10 described herein. While this pulbication in another figure demonstreates average pressure of about 30 psi, this seal 10 is also capable of maintaining an average cement pressure of at least about 50 pounds psi. Finally, another figure in this publication shows that a peak intramedullary pressure of about 60 psi is possible using the proximal femoral seal 10 as compared to the manual technique sand use of a solid seal. Yet, peak pressures of up to 100 psi have been achieved using the proximal femoral seal 10 described herein.

Variations of the above described method which involve minor changes in the sequencing of steps are clearly contemplates to be within the scope of the present invention. In addition, minor variations in the design, angles or materials of the proximal femoral seal fo the present invention are also contemplated to be within the scope of the present invention. These modifications and variations of the above invention may be made without departing from it spirit and scope, as will become apparent to those skilled in the art. The specific embodiments described herein are offered by way of example only, and the ivnention is limited only by the terms of the appended claims.

I claim:

1. Apparatus for introducing cement into a bone canal through an opening in the bone, comprising:
   (a) body member having a passageway of predetermined cross-section extending therethrough for passage of cement;
   (b) generally annular wall member extending from said body member and defining an outer surface at least a portion of which is elastically expandable and is configured and dimensioned so as to be capable of extending into the bone canal, said outer surface adapted to provide a contacting seal along a length of the inner walls of the bone canal; and
   (c) chamber defined by said annular wall emmber, said chamber having a cross-section greater than said predetermined cross-section of said passageway and communicating with said passageway and relatively stationary with said bone canal such that cement, upon its introudction into said bone canal, will also fill said chamber and cause said elastically expandable portion of said annular wall to expand so as to aid in maintaining said seal.

2. Apparatus for injecting cement into the bone canal through an opening in the bone, comprising:

(a) body member having a passageway of predetermined cross-section extending therethrough for passage of cement;

(b) Generally elastically expandable annular wall member extending from said body member and defining with said body member a generally continuous outer surface which is configured and dimensioned such that at least a portion of said ourter surface corresponds anatomically to a portion of the bone canal adjacent the opening so as to be capable of extending into the bone canal, said otuer surface adapted to provide a contacting seal along a length of the inner walls of the bone canal; and (c) chamber defined by sadi annular wall member and said body member, said chamber having a crossection greater than said predetermiend cross-section of said passageway and communicating with said passageway and relatively stationary with said bone canal such that cement upon its injection into said bone canal will also fill said chamber so as to expand said elastically expandable annular wall member and thus maintain said seal and aid in the penetration of cement into the bone with the canal.

3. a proximal femoral sealing device for seating within the medullary canal of a prepared proximal end of a femur and for injecting cement under pressure into the medullary canal, comprising:

(a) body member having a passageway of predetermined cross-section extending therethrough for passage of cement;

(b) generally elastically expandable annular wall member extending from said body emmber and defining said body member an outer surface which is anatomically shaped and conforms generally along the vertical and horizontal axes of the body member to the exposed internal endosteal surface shape of the proximal end of the medullary canal of the femur; and (c) chamber defined by said elastically expandable wall member and said body member, said chamber having a cross-section greater than said predetermined cross-section of said passageway and opening onto and communicating at one end with said proximal end of said medullary canal, the other, opposite end opening onto and communicating with the distal end of said passageway, said chamber further having a generally rounded-trapazoidal cross-sectional configuration defined by said elastically expandable wall member which is capable of expanding under pressure of cement within said chamber against the exposed internal endosteal surface of the medullary canal so as to form a pressurization cement seal.

4. The seal of claim 3 wherein said anatomically shaped outer surface generally corresponds to the outer surface shape fo a broach utilized to expose the endosteal surface of the medullary canal.

5. The seal of calim 3 wherein said anatomically shaped outer surface generally corresponds to the natural internal surface shape fo the medullary canal.

6. The seal of claim 3 wherein said anatomically shaped otuer surface further comprises a pluraltiy of ridges.

7. The seal of claim 6 wherein said plurality of ridges are dimensioned and configured so that leading edges thereof contact the exposed internal endosteal surface.

8. The seal of claim 3 wherein the proximal end of said anatomically shaped outer surface is wider than the distal end along a cross-section of the vertical axis of the seal.

9. The seal of claim 3 wherein the portion of said anatomically shaped outer surfae adjacent with the lateral side of the medullary canal is aligned at an angle from about 1° to about 4° in from the vertical axis of said seal towards the wall on the medial side of the said medullary canal.

10. The seal of claim 3 wherein the portion of said substantially anatomically shaped outer surface on the medial side of said medullary canal ranges from a straight surface to one which is curved from the proximal to distal end of said substantially anatomically shaped outer surface.

11. The seal of claim 3 wherein said wall member is thicker at the aproximal end of said chamber than at the distal end of said chamber.

12. The seal of claim 11 wherein said wall member tapers to reduce in thickness from said proximal end to said distal end.

13. The seal of claim 3 wherein said substantially anatomically shaped outer surface which ends at the distal end of the seal is aligned at an angle of about 0° to about 20° away from the horizontal axis of the seal toward said proximal end of the seal.

14. The seal of claim 3 wherein the exterior lateral portion of said wall member is aligned at about 10° from the vertical axis of the seal, the interior lateral and interior medial portions being aligned parallel to each other and with the end of the interior medial portion of the wall being located closer to the vertical axis than the interior lateral portion of the wall.

15. The seal of claim 3 wherein the anterior and posterior portions of said wall member between the medial and lateral portions are aligned on the horizontal axis at an angle from about 10° to about 12° away from the transverse axis, said anterior and posterior portions being closer together at said medial portion than at said lateral portion.

16. The seal of claim 3 wherein said passageway is centrally disposed in the body member.

17. The seal of claim 3 wherein said passageway is dimensioned and configured to receive a nozzle for injection of cement.

18. The seal of claim 3 wherein a medial portion of the upper portion of said body member is inset from the medial wall of said anatomically shaped outer surface.

19. The seal of claim 3 wherein said passageway is cylindrical in shape.

20. The seal of claim 3 wherein said passageway narrows to form a gasket-seal so as to restrain a cement nozzle inserted through said passageway.

21. The seal of claim 20 wherein said gasket-seal is disposed adjacent the proximal end of said chamber.

22. The seal of claim 20 wherein said gasket-seal is disposed between the proximal and distal ends of said passageway.

23. The seal of claim 3 wherein said body member and flexible annular wall member are formed of a medical grade elastomer.

24. The seal of claim 3 wherein said body member and flexible annular wall member are integrally formed of silicone.

* * * * *